United States Patent [19]

Liao et al.

[11] 4,290,769
[45] Sep. 22, 1981

[54] STABILIZED ROMANOWSKY STAIN SOLUTION

[75] Inventors: John C. Liao; Chittaranjan P. Patel, both of Elkhart; John L. Ponzo, Mishawaka, all of Ind.

[73] Assignee: Miles Laboratories, Inc., Elkhart, Ind.

[21] Appl. No.: 196,365

[22] Filed: Oct. 14, 1980

[51] Int. Cl.³ ............................................. C09B 67/00
[52] U.S. Cl. .......................................... 8/602; 8/506; 8/620; 8/638; 8/644
[58] Field of Search ................... 8/506, 602, 620, 638, 8/644

[56] References Cited

PUBLICATIONS

J. W. Gilliland et al., Stain Technology, 1979, 54, (No. 3), pp. 141-150.
W. W. Dean et al., Stain Technology, 1977, 52, (No. 1), pp. 35-46.
E. Gurr et al., in "The Chemistry of Synthetic Dyes," vol. VII, (Venkataraman: Editor), Academic Press, 1974, p. 288.

*Primary Examiner*—A. Lionel Clingman
*Attorney, Agent, or Firm*—Jerome L. Jeffers

[57] ABSTRACT

The present invention is a stabilized Romanowsky type stain solution. The stain solution which comprises azures, Methylene Blue and an eosin dye in methanol is stabilized by the addition thereto of an ammonium halide, a primary, secondary or tertiary alkylamine hydrohalide or a combination thereof.

11 Claims, No Drawings

STABILIZED ROMANOWSKY STAIN SOLUTION

BACKGROUND OF THE INVENTION

This invention relates to blood staining systems and more particularly to the stabilization of Romanowsky type stains. Romanowsky type stains, e.g., Wright's solution and Giemsa's solution, comprise methylene blue and an eosin dye in methanol solution along with other allied dyes. Typical allied dyes include Azure A, Azure B and Azure C.

In order to employ such a stain it is usually necessary to prepare a solution of the dry stain in methyl alcohol and apply the solution to a blood smear or the like. Next a buffer solution and a rinse solution are added stepwise to the stained smear until a visable physical change occurs.

The presence of a second dye in addition to methylene blue, particularly Eosin Y, is desirable to enhance the staining qualities of the solution. Other allied dyes, i.e., Azure A, Azure B and Azure C are also desirable for their enhancement of the solution's ability to stain the blood smear. The standard way of using the dye is to form the solution and allow it to stand for a period of time. The azure dyes in stain powder are not very soluble in methanol. However, Methylene Blue degrades into azures in the presence of eosin upon aging in solution. It will normally take about two weeks of standing for optimal staining results to be achieved. Unfortunately, the dyes continue to oxidize, and the resultant oxidation products render the solution unsuitable for the intended purpose. In addition, random precipitation in the stain solution upon aging results in poor stain quality. Thus, while the stain solution takes about two weeks to become fully effective, it has a shelf life of only about 3 to approximately 12 months.

It would be desirable, and it is an object of the present invention to provide a method for the stabilization of the above described Romanowsky staining solutions.

It is a further object to provide a stabilized Romanowsky stain solution having a significantly increased shelf life.

SUMMARY OF THE INVENTION

The present invention is a method for the stabilization of a Romanowsky type stain which comprises Methylene Blue and an eosin dye in methanol solution. The method involves the introduction of a stabilizing amount of an ammonium halide; a primary, secondary or tertiary alkylamine hydrohalide or a combination thereof in which the alkyl chains contain from 1 to 6 carbon atoms, said halide being selected from the group of chloride, bromide or iodide.

DETAILED DESCRIPTION

The most widely used Romanowsky type stains are known as Wright's and Giemsa's solutions. Both comprise azures, Methylene Blue and an eosin dye in methanol solution; the former having an absorbence ratio of azures and Methylene Blue to eosin of about 1.70 to 2.10 with the latter having an absorbence ratio of about 1.70 to 1.80 (absorbence ratio equals $A_{650}/A_{525}$).

Reproducible stain performance, constant stain absorbence and absorbence ratios (as determined by a spectrophotometer) and the absence of precipitates are indicators of a stable stain solution. Various additives were found to improve the stability of the solutions under consideration which stability improved in proportion to the amount of additive used. Those stabilizers found to be effective are the ammonium halides, i.e., ammonium chloride, ammonium bromide and ammonium iodide as well as the primary, secondary and tertiary alkylamine hydrohalides in which the alkyl chains contain from 1 to 6 carbon atoms and the halide is chloride, bromide or iodide. Those alkylamine hydrohalides suitable for use in the present invention include hydrochlorides of diethylamine, dipropylamine, dibutylamine, tripopylamine and tributylamine. The hydrobromides and hydroiodides of these amines may also be used. In addition to providing reproducible stain performance and constant absorbence, stain precipitation problems were eliminated in the presence of secondary and tertiary alkylamine (except dimethylamine and trimethylamine) hydrochlorides.

The amount of stabilizing additive is not critical although an amount of 0.1 to 1.2% (w/w based on the solution) is preferred. The use of diethylamine hydrochloride at a concentration of about 0.6% (w/w) is particularly effective in providing the desired stabilization at the lowest cost. In addition, this formulation provides good stain performance, is highly soluble and is very effective in reducing component changes. Furthermore, the precipitation problems of stain solutions are completely eliminated and the shelf life of the stain containing this stabilizer is increased to 2.5–3 years.

EXAMPLE

A solution was prepared by dissolving 3.0 gm of Wright's stain powder (MCB, Norwood, Ohio) in 1,000 ml. of methanol. The composition of the powder was 37% Eosin Y, 33% Methylene Blue and 30% azures and azure eosinate.

After 20 minutes of shaking at room temperature and allowing the solution to stand for 2 weeks, undissolved powder was removed by filtration. The filtered stain solution was then diluted to 0.575 absorbence at 650 nm (Beckman Spectrophotometer) before addition of a candidate stabilizer.

The absorbence ratio ($A_{650}/A_{525}$) of a stressed Wright's stain solution with the addition of a particular stabilizer is set out in Table I. These ratios were obtained by running the spectrophotometric scans of stain solutions after a 1/400 dilution. The ratio of absorbence of 650 nm to 525 nm (peak maximum at or near 525 nm) was designated for monitoring stability of the stain solutions. The ratio was found to decrease with the degradation of stain.

From Table I the following conclusions can be drawn:

The control stain solutions (no stabilizer added) degrade slowly at 23° C. and rapidly at 50° C. upon aging as indicated by the decrease in absorbence ratio. The stabilizers reduce the rate of stain degradation. The stabilized stain solutions have relatively higher absorbence ratios than the corresponding control under the same stress conditions (i.e., temperature and age).

Table II shows a typical example of a stabilized stain solution. This solution with the addition of 0.6% $Et_2NH_2+Cl$ produced good staining performance both before and after stress at 50° C. for 28 days. The control solution produced unbalanced staining after stress at 50° C. for 28 days. The result shows that the stabilizer in the stain solution has no detrimental effect in the staining of blood smears. The stain shelf life is prolonged with the addition of the stabilizer.

TABLE I

Absorbance Ratio ($A_{650}/A_{525}$) of Stressed Wright's Stain Solution with the Addition of Stabilizer

| | Set 1 | | | | Set 2 | | | | Set 3 | | | | Set 4 | | | |
|---|---|---|---|---|---|---|---|---|---|---|---|---|---|---|---|---|
| | Control | | 0.2% NH$_4$Br | | Control | | 0.3% C$_6$NH$_3{}^+$Cl$^-$ | | Control | | 0.6% Et$_2$NH$_2{}^+$Cl$^-$ | | Control | | 0.3% Et$_3$NH$^+$Cl$^-$ | |
| Time, day | 23° | 50° | 23° | 50° | 23° | 50° | 23° | 50° | 23° | 50° | 23° | 50° | 23° | 50° | 23° | 50° |
| | Ratio | | | | | | | | | | | | | | | |
| 0 | 1.80 | 1.80 | 1.80 | 1.80 | 1.76 | 1.76 | 1.76 | 1.76 | 2.00 | 2.00 | 2.00 | 2.00 | 2.06 | 2.06 | 2.06 | 2.06 |
| 7 | 1.75 | 1.30 | 1.80 | 1.59 | 1.73 | 1.29 | 1.74 | 1.65 | 1.96 | 1.45 | 2.00 | 1.89 | 2.01 | 1.42 | 2.03 | 1.78 |
| 28 | 1.66 | 0.86 | 1.72 | 1.24 | 1.66 | 0.83 | 1.75 | 1.58 | 1.84 | 0.86 | 1.99 | 1.54 | 1.88 | 0.90 | 1.97 | 1.32 |

TABLE 2

The Differential Staining Performance of Stain Solutions on Blood Smears With and Without the Addition of Diethylamine Hydrochloride.

A. Stain solutions before stress

| | Neutrophils | | Eosinophils | | Lymphocytes | | Monocytes | | Red Blood Cells | Platelets |
|---|---|---|---|---|---|---|---|---|---|---|
| Et$_2$NH$_2{}^+$Cl$^-$ | N** | C** | N | C | N | C | N | C | | |
| | Score* | | | | | | | | | |
| 0% | 5.0 ± 0.0 | 4.0 ± 0.0 | 4.3 ± 0.3 | 4.5 ± 0.0 | 5.0 ± 0.0 | 5.0 ± 0.0 | 4.5 ± 0.0 | 4.3 ± 0.3 | 3.3 ± 0.3 | 3.7 ± 0.3 |
| 0.6% | 4.8 ± 0.3 | 4.2 ± 0.3 | 4.0 (n = 1) | 4.5 (n = 1) | 4.8 ± 0.3 | 4.8 ± 0.3 | 4.5 ± 0.5 | 4.5 ± 0.5 | 3.3 ± 0.3 | 3.7 ± 0.3 |

*Average ± s (n = 5). Score: 5, excellent; 4, good; 3, satisfactory and <3, not satisfactory.
**N = nucleus; C = cytoplasm

B. Stain solutions after stress at 50° C. for 28 days

| | Neutrophils | | Eosinophils | | Lymphocytes | | Monocytes | | Red Blood Cells | Platelets |
|---|---|---|---|---|---|---|---|---|---|---|
| Et$_2$NH$_2{}^+$Cl$^-$ | N** | C** | N | C | N | C | N | C | | |
| | Score* | | | | | | | | | |
| 0% | 4.0 ± 0.0 | 3.7 ± 0.3 | 4.0 ± 0.7 | 4.6 ± 0.5 | 3.1 ± 0.2 | 3.1 ± 0.2 | 2.4 ± 0.5 | 2.4 ± 0.5 | 3.6 ± 0.7 | 3.2 ± 0.3 |
| 0.6% | 5.0 ± 0.0 | 4.6 ± 0.4 | 5.0 ± 0.0 | 5.0 ± 0.0 | 5.0 ± 0.0 | 5.0 ± 0.0 | 5.0 ± 0.0 | 4.0 ± 0.3 | 4.9 ± 0.3 | 4.6 ± 0.3 |

* and **same as above

What is claimed is:

1. In combination with a Romanowsky type stain comprising azures, Methylene Blue and an eosin dye in methanol solution, the improvement which comprises the presence of a stabilizing amount of an ammonium halide, a primary, secondary or tertiary alkylamine hydrohalide or a combination thereof in which the alkyl chains contain from 1 to 6 carbon atoms, said halide being selected from the group of chloride, bromide or iodide.

2. The improved stain solution of claim 1 wherein the stabilizing additive is selected from the group of the hydrochloride, hydrobromide or hydroiodide of diethylamine, dipropylamine, dibutylamine, tripropylamine or tributylamine.

3. The improved stain of claim 2 wherein the hydrochloride salt of the alkylamine is employed as stabilizer.

4. The improved stain of claim 1 wherein the stabilizer is present in an amount of from 0.1 to 1.2 weight percent of the solution.

5. The improved stain of claim 1 wherein the stabilizing material is diethylamine hydrochloride.

6. The improved stain of claim 5 wherein the diethylamine hydrochloride is present in an amount of from 0.1 to 1.2 weight percent of the solution.

7. The improved stain of claim 5 wherein the diethylamine hydrochloride is present in the amount of about 0.6 weight percent of the solution.

8. A method for the stabilization of a Romanowsky type stain comprising azures, Methylene Blue and an eosin dye in methanol solution which comprises adding to said solution a stabilizing amount of an ammonium halide, a primary, secondary or tertiary alkylamine hydrohalide or a combination thereof in which the alkyl chains contain from 1 to 6 carbon atoms, said halide being selected from the group of chloride, bromide or iodide.

9. The method of claim 8 wherein the additive is diethylamine hydrochloride.

10. The method of claim 9 wherein the diethylamine hydrochloride is added in an amount of from 0.1 to 1.2 weight percent of the solution.

11. The method of claim 10 wherein the amount is about 0.6 weight percent of the solution.

* * * * *